United States Patent
Fujita et al.

(10) Patent No.: US 10,281,400 B2
(45) Date of Patent: May 7, 2019

(54) METHOD FOR ENHANCING LUMINESCENCE, SUBSTANCE DETECTION METHOD, SUBSTANCE DETECTION APPARATUS, AND LUMINESCENCE ENHANCER

(71) Applicant: SONY CORPORATION, Tokyo (JP)

(72) Inventors: Shuji Fujita, Tokyo (JP); Kyohei Yoshimitsu, Tokyo (JP); Seiji Yamada, Kanagawa (JP); Daisuke Yamaguchi, Kanagawa (JP); Yoshio Goto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/741,882

(22) PCT Filed: May 9, 2016

(86) PCT No.: PCT/JP2016/063715
§ 371 (c)(1),
(2) Date: Jan. 4, 2018

(87) PCT Pub. No.: WO2017/010152
PCT Pub. Date: Jan. 19, 2017

(65) Prior Publication Data
US 2018/0202933 A1  Jul. 19, 2018

(30) Foreign Application Priority Data
Jul. 13, 2015  (JP) .................................. 2015-139816

(51) Int. Cl.
*C09K 11/02* (2006.01)
*C09K 11/06* (2006.01)
(Continued)

(52) U.S. Cl.
CPC ....... *G01N 21/6428* (2013.01); *C09B 23/086* (2013.01); *C09K 11/02* (2013.01);
(Continued)

(58) Field of Classification Search
CPC ....... C09B 23/086; C09K 11/02; C09K 11/06; G01N 21/64; G01N 21/6428; G01N 33/533
See application file for complete search history.

(56) References Cited

U.S. PATENT DOCUMENTS

| | | | |
|---|---|---|---|
| 2013/0075657 A1* | 3/2013 | Zhou ................. | C09K 11/7734 252/301.4 F |
| 2015/0053916 A1* | 2/2015 | Pickett ................. | C09K 11/565 257/13 |
| 2015/0255688 A1* | 9/2015 | Stoll .................... | C09K 11/565 257/98 |

FOREIGN PATENT DOCUMENTS

| | | |
|---|---|---|
| JP | 02-179451 A | 7/1990 |
| JP | 2008-298505 A | 12/2008 |

(Continued)

OTHER PUBLICATIONS

International Search Report and Written Opinion of PCT Application No. PCT/JP2016/063715, dated Jun. 28, 2016, 06 pages of ISRWO.

*Primary Examiner* — Mark R Gaworecki
(74) *Attorney, Agent, or Firm* — Chip Law Group

(57) ABSTRACT

A method for enhancing luminescence of a luminous material, a substance detection method, a substance detection apparatus, and a luminescence enhancer are provided. A method for enhancing luminescence of a luminous material, the method including: holding, in a luminescence detection unit, the luminous material and a white colloidal particle both contained in a liquid; and irradiating the luminescence detection unit with light, in which the luminescence detec-
(Continued)

tion unit has an inner diameter of 300 μm or less in an optical axis direction.

9 Claims, 3 Drawing Sheets

(51) Int. Cl.
  *G01N 21/64* (2006.01)
  *G01N 33/533* (2006.01)
  *C09B 23/08* (2006.01)
(52) U.S. Cl.
  CPC .............. *C09K 11/06* (2013.01); *G01N 21/64* (2013.01); *G01N 33/533* (2013.01)

(56) References Cited

FOREIGN PATENT DOCUMENTS

| | | |
|---|---|---|
| JP | 2010-145272 A | 7/2010 |
| WO | 2013/109963 A1 | 7/2013 |

\* cited by examiner

METHOD FOR ENHANCING LUMINESCENCE, SUBSTANCE DETECTION METHOD, SUBSTANCE DETECTION APPARATUS, AND LUMINESCENCE ENHANCER

CROSS REFERENCE TO RELATED APPLICATIONS

This application is a U.S. National Phase of International Patent Application No. PCT/JP2016/063715 filed on May 9, 2016, which claims priority benefit of Japanese Patent Application No. JP 2015-139816 filed in the Japan Patent Office on Jul. 13, 2015. Each of the above-referenced applications is hereby incorporated herein by reference in its entirety.

TECHNICAL FIELD

The present invention relates to a method for enhancing luminescence, a substance detection method, a substance detection apparatus, and a luminescence enhancer.

BACKGROUND ART

Detection of a detection target labeled with a fluorescent pigment is performed such that the fluorescent pigment is irradiated with excitation light having a specific wavelength, fluorescence emitted from the fluorescent pigment is received, and thus the detection target is detected. In this process, a higher fluorescence intensity makes the detection of the target easier. It has been desired to enhance the detection sensitivity.

Accordingly, to enhance the detection sensitivity, a method has conventionally been used in which, for example, a reflector is provided on an inner wall of the detection unit to cause the reflector to reflect fluorescence emitted from the fluorescent pigment, and thus to condense the fluorescence onto a light reception unit.

Meanwhile, a method for enhancing fluorescence has recently been developed in which a mixture of a fluorescent pigment-containing solution and a fluorescence-enhancing diluent is applied to a biological tissue section to fluorescently stain the biological tissue section, and thus enhanced fluorescence is obtained (Patent Document 1).

This method uses, as the fluorescent pigment, indocyanine green, which is a near-infrared fluorescent pigment, and uses, as the fluorescence-enhancing diluent, an emulsion such as milk, formula milk, fat emulsion, soybean oil, or egg phospholipid, or Intralipid, Lyposyn, Nutralipid, Soyacal, Travamulsion, SOMFlipid, Clinoleic, or Lipovenoes, which are registered trademarks.

Patent Document 1 mentioned above describes that when a biological tissue section was stained with a mixture of a fluorescent pigment and a fluorescence-enhancing diluent, and was then irradiated with near-infrared radiation, an observation showed that the fluorescence intensity was increased 5 to 20 times higher than the fluorescence intensity obtained without addition of the fluorescence-enhancing diluent.

CITATION LIST

Patent Document

Patent Document 1: WO 2013/109963 A

SUMMARY OF THE INVENTION

Problems to be Solved by the Invention

However, the technology disclosed in Patent Document 1 mentioned above uses a fluorescence-enhancing diluent containing emulsion of particles having a particle size less than 100 nm, and a near-infrared fluorescent pigment, only to stain biological tissue.

It is a primary object of the present technology to provide a method for enhancing luminescence of a luminous material, a substance detection method, a substance detection apparatus, and a luminescence enhancer, each providing more than staining biological tissue.

Solutions to Problems

That is, the present technology provides a method for enhancing luminescence of a luminous material, the method including:

holding, in a luminescence detection unit, the luminous material and a white colloidal particle both contained in a liquid; and irradiating the luminescence detection unit with light, in which the luminescence detection unit has an inner diameter of 300 µm or less in an optical axis direction.

The light may be UV light and/or visible light.

The luminous material may be a fluorescent pigment or a fluorescent bead.

The colloidal particle may be held in the liquid in the luminescence detection unit at a concentration ranging from 5 percent by mass (mass %) to 20 mass %.

In addition, the colloidal particle may have a particle size ranging from 0.1 µm to 1 µm.

Furthermore, the colloidal particle may be at least one type of particle selected from the group consisting of latex, acryl, silicone, polyurethanes, polyvinyls, polylactic acid, polyacetic acid, PVDF, PFA, PTFE, polycarbonates, polyolefins, polyethylene glycols, polyethylenes, nylons, lipids, proteins, nucleic acids, liposomes, and microorganism cells.

In addition, the present technology provides a substance detection method including:

holding, in a luminescence detection unit, a detection target material labeled with a luminous material, and a white colloidal particle, both contained in a liquid; and irradiating the luminescence detection unit with light, in which the luminescence detection unit has an inner diameter of 300 µm or less in an optical axis direction.

In addition, the present technology provides a substance detection apparatus including:

a luminescence detection unit having an inner diameter of 300 µm or less in an optical axis direction, the luminescence detection unit capable of holding a luminous material and a white colloidal particle both contained in a liquid;

a light source unit for irradiating the luminescence detection unit with light; and a light reception unit that receives light emitted from the luminous material.

Furthermore, the present technology provides a luminescence enhancer containing, as an active ingredient, a white colloidal particle having a particle size ranging from 0.1 µm to 1 µm.

Effects of the Invention

The present technology can significantly enhance luminescence of a luminous material in liquid.

Note that the effects described here are not limiting, and may be any of the effects described in the present disclosure.

MODE FOR CARRYING OUT THE INVENTION

Figure 1:
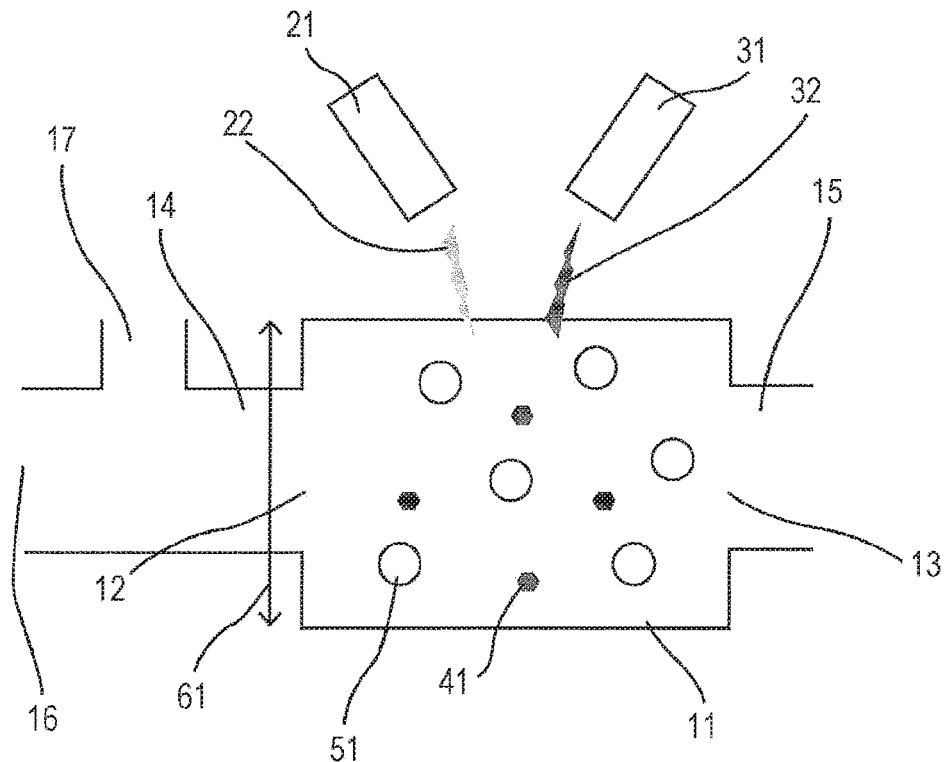
FIG. 1 is a schematic diagram of a luminescence detection device according to the present technology.

A preferred mode of practicing the present technology will be described below. Note that the embodiment described below is intended only to provide a typical embodiment of the present technology, and thus should not be construed as limiting the scope of the present technology. The description will be given in the order set forth below.
1. Method for enhancing luminescence of a luminous material
   (1) Luminous material
   (2) White colloidal particles
   (3) Luminescence detection unit
   (4) Light irradiation
   (5) Light reception
2. Substance detection method
   (1) Detection target
   (2) Method for detecting a substance
3. Substance detection apparatus
   (1) Luminescence detection unit
   (2) Light source unit
   (3) Light reception unit
   (4) Application of substance detection apparatus
4. Luminescence enhancer
5. Experimental examples
   (A) Increase in fluorescence intensity provided by white colloidal particles
   (B) Study of inner diameter of luminescence detection unit
   (C) Study of excitation wavelength and emission wavelength of fluorescent beads
   (D) Study of excitation wavelength and emission wavelength of fluorescent molecules

1. Method for Enhancing Luminescence of a Luminous Material

The present inventors have found that dispersion of a fluorescent pigment in liquid followed by suspension of white colloidal particles in that liquid increases the fluorescence intensity under specific conditions in spite of a reduction in the transparency of the liquid.

The present technology has been developed on the basis of this finding, and is a technology in which liquid containing both a luminous material and white colloidal particles are fed into a luminescence detection unit having an inner diameter of 300 μm or less, and the luminescence detection unit is irradiated with light to enhance luminescence of the luminous material.

(1) Luminous Material

The luminous material for use in the present technology is a material that absorbs energy and emits the energy as light. The present technology utilizes photoluminescence, in which light, such as, in particular, UV light, visible light, and infrared light, is used as a stimulus, and energy of such light is absorbed to emit light.

Examples of the luminous material include dye compounds that emit fluorescence or phosphorescence. Specific examples of the dye compounds that emit fluorescence or phosphorescence include commercially available fluorescent pigments, such as Alexa Fluor, MegaStokes Dye, Oyster, HiLyte Fluor, Pacific Blue, Coumarin, BODIPY FL, Oregon Green, Pacific Oarnge, Texas Red, DyLight, AMCA, Royal Blue, ATTO, FAM, MFP, Spectrum Green, NorthernLight, TAMRA, PE, ROX, Spectrum Red, ECD, Phycocyanin, Quantum Red, PerCP, IRDye, DY, R-Phycoerythrin, Allophycocyanin, DIPI, Nile Blue, Europium, Dragon Green, Flush Red, Cy pigment, merocyanine, rubrene, 5,12-bis(phenylethynyl)naphthacene, pyranine, umbelliferone, SYBR Green, ethidiumbromide, fluorescein, rhodamine, TRITC, and stilbene.

In addition, the luminous material of the present technology also includes derivatives of the above-listed dye compounds; fluorescent proteins such as CFP, GFP, RFP, and UnaG; nucleic acids (DNA, RNA, and PNA), amino acids, peptides, and antibodies stained with various fluorescent pigments; and fluorescent beads. However, the present technology is not limited thereto.

A luminous material has a material-specific excitation wavelength and a material-specific fluorescent wavelength. The dye compounds that emit fluorescence or phosphorescence described above mostly have an excitation wavelength ranging from about 400 to 800 nm, and a fluorescent wavelength ranging from 420 to 820 nm. Thus, it is preferred that the luminous material be irradiated with excitation light suitable for that luminous material within the wavelength range upon light irradiation described below.

Note that the luminous material for use in the present technology may be contained alone in liquid, or may be contained in abound form with the detection target after allowing contact between the luminous material and the detection target in the liquid.

In addition, the luminous material may be fixed, for example, on a plate, in a well, on a bead, or inside the luminescence detection unit described below.

(2) White Colloidal Particles

Colloidal particles are visually perceived in various colors, such as black, red, purple, blue, yellow, and white. However, the colloidal particles for use in the present technology are those perceived as white or near white. For example, combination of black colloidal particles, such as carbon particles, with the luminous material in the liquid did not provide enhancement of light emitted from the luminous material.

The white colloidal particles for use in the present technology are fine particles dispersible in a liquid dispersant. Colloidal particles are typically spherical, but the colloidal particles may also be non-spherical.

The particle size of the white colloidal particles for use in the present technology is not particularly limited, but for example, in a range of from 0.1 μm to 1 μm. Particles having a particle size not as low as less than 0.1 μm provide the advantageous effect of the present technology to a sufficient degree. In addition, particles having a particle size greater than 1 µm may fail to provide advantageous effects of colloidal particles.

The term "particle size" as used in the present technology refers to average diameter. The average diameter may be determined by selecting and using a major axis length, a minor axis length, a diameter in specified direction, a diameter of area bisector in a specified direction, a maximum width in a specified direction, a biaxial average diameter, a triaxial average diameter, an equivalent cube diameter, an equivalent circle diameter, an equivalent area diameter, an equivalent volume diameter, or the like, depending on the shape of the colloidal particles.

Examples of the white colloidal particles include milk, skim milk, latex, acryl, silicone, polyurethanes, polyvinyls, polylactic acid, polyacetic acid, PVDF, PFA, PTFE, polycarbonates, polyolefins, polyethylene glycols, polyethylenes, nylons, lipids, proteins, nucleic acids, liposomes, and microorganism cells. However, the present technology is not limited to these materials.

The concentration of the white colloidal particles in the liquid is not particularly limited, but is preferably in a range of from 5 mass % to 20 mass %. Such concentration may significantly enhance the emission light from the luminous material also contained in the liquid. A concentration less than 5 mass % or greater than 20 mass % may fail to provide the advantageous effects of the present technology.

(3) Luminescence Detection Unit

The luminescence detection unit for use in the present technology has an inner diameter of 300 µm or less in an optical axis direction when light is irradiated from the light source unit described later herein. An inner diameter of 300 µm or less can significantly enhance the emission light from the luminous material when the luminescence detection unit holds both a luminous material and a white colloid, and thus the light reception unit described later herein can receive strong emission light. This configuration can significantly improve the detection sensitivity.

In addition, the inner diameter is preferably 1 µm or more. Colloidal particles may have a particle size of about 1 µm, and therefore, it is intended to allow such colloidal particles to be contained in the luminescence detection unit.

The luminescence detection unit may have any shape as long as the luminescence detection unit has at least one portion providing an inner diameter (depth) of 300 µm or less in the optical axis direction during light irradiation. The shape may be, for example, a cylinder, a circular truncated cone, an inverted circular truncated cone, an elliptic cylinder, an elliptic column, an inverted elliptic truncated cone, a sphere, or an ellipsoid, or one of these shapes having a recess and/or salient thereon.

At least one liquid channel is preferably attached to the luminescence detection unit to allow the liquid containing the luminous material and/or the white colloidal particles to flow in and out.

Moreover, the liquid may further contain the detection target in addition to the luminous material and/or the white colloidal particles.

For example, upstream of and/or inside the luminescence detection unit, the luminous material and the detection target bond together, and the remaining unbound luminous material are thus removed, thereby allowing the bound material of the luminous material and the detection target to remain. The luminescence detection unit also contains the white colloidal particles, which contributes to enhancing the emission light from the luminous material upon irradiation of the luminescence detection unit with light. Thus, even when the concentration of the detection target is low, the detection target can be readily detected.

(4) Light Irradiation

The present technology can select the type of the light to use depending on the type of the luminous material used. The light may have a wavelength identical to the excitation wavelength of the luminous material, and accordingly, the excitation wavelength specific to a dye compound listed above, for example, may be selected. Depending on the dye compound used, near-infrared light, UV light, visible light, or the like may be selected. Specifically, light having a wavelength ranging from about 400 to 800 nm corresponding to visible light may be used.

The light is preferably irradiated in a constant direction, at a constant wavelength, and at a constant light intensity. The light source used may be a laser, such as an argon ion laser, a helium-neon laser, a dye laser, or a krypton laser; an LED; a mercury lamp; or the like.

In addition, for irradiation of the light, a dichroic element, a condenser lens, an optical filter, and/or the like may be provided as appropriate to adjust the angle of incident light, light transmittance, and/or the like.

(5) Light Reception

The light may be received using a photodetector, such as, for example, a spectral luminance meter, a CCD, a CMOS, or the like.

In addition, it is preferable that only light having a specific wavelength emitted from the luminous material be received, but the manner of the light reception is not limited thereto. Light having wavelengths other than a specific wavelength can be cut off using, for example, an infrared cut-off filter, a visible light cut-off filter, a UV cut-off filter, or the like.

2. Substance Detection Method

The substance detection method of the present technology is a method for detecting a detection target material including labeling a detection target material in liquid with a luminous material, containing both the detection target material labeled with the luminous material and white colloidal particles in the luminescence detection unit, irradiating the luminescence detection unit with light, and receiving enhanced emission light emitted from the luminous material.

(1) Detection Target

The detection target in the present technology is not particularly limited, and may be any material that can be labeled with the luminous material described above. Examples thereof include proteins, peptides, glycoproteins, nucleic acid molecules, precursors thereof, and products formed by decomposition thereof. Such examples specifically include viruses, bacteria, hormones, cytokines, antigens, antibodies, enzymes, and materials that can be obtained from a biological internal or external tissue (e.g., a surface of dermal tissue, an inside of tissue, etc.).

The detection target is dispersed in liquid. The concentration thereof is not particularly limited. High sensitivity of the substance detection method according to the present technology enables merely a trace amount of the substance to be detected to a sufficient degree as compared to a conventional technology.

(2) Method for Detecting a Substance

The method for detecting a substance of the present technology is performed, for example, as follows.

(i) Add the luminous material to the sample. This causes the luminous material to bind to the detection target contained in the sample in a proportion correlated to the amount of the detection target, and thus a detection target labeled with the luminous material is formed.

(ii) Remove the unbound portion of the luminous material as needed.

(iii) Add the white colloidal particles. Preferably, the content thereof is in a range of from 5 mass % to 20 mass % with respect to the liquid. This step further disperses the detection target labeled with the luminous material.

(iv) Charge the luminescence detection unit with a mixture of the detection target labeled with the luminous material and the white colloidal particles. Note that the above step (iii) of adding the white colloidal particles may be performed before or after the charging of the luminescence detection unit with the detection target labeled with the luminous material.

(v) Irradiate the luminescence detection unit with light having a wavelength suitable for the luminous material used for labeling.

(vi) Receive emission light emitted from the luminous material.

(vii) Determine whether the detection target is present or absent on the basis of the emission light intensity. Moreover, a process may further be performed that includes preparing in advance a reference sample for calibration, obtaining a calibration curve using the intensity of the emission light received, and thus quantifying the detection target.

3. Substance Detection Apparatus

The luminescence detection device of the present technology is characterized by including, at least, a light source unit, a luminescence detection unit, and a light reception unit, and is characterized in that the luminescence detection unit has an inner diameter of 300 µm or less in an optical axis direction from the light source unit.

An example of the luminescence detection device of the present technology will be described below with reference to FIG. 1.

(1) Luminescence Detection Unit

A luminescence detection unit 11 is a cell formed to have an inner diameter 61 of 300 µm or less in an optical axis direction of light irradiated from a light source unit 21. The cell is made of a material such as, for example, quartz glass, borosilicate glass, polymethyl methacrylate, polydimethylsiloxane, or polyethylene terephthalate. The luminescence detection unit 11 has an inlet 12 and an outlet 13 formed therein, from which flow channels 14 and 15 respectively extend upstream and downstream thereof. A sample feed port 16 is provided upstream of the flow channel 14 to feed a sample containing a luminous material 41 or a detection target labeled with the luminous material. A white colloidal particle feed port 17 is provided between the flow channel 14 and the luminescence detection unit 11. White colloidal particles 51 are fed through the white colloidal particle feed port 17 so that the final concentration in the luminescence detection unit 11 will be in a range of from 5 mass % to 20 mass %.

In a downstream portion of the flow channel 15 extending from the outlet 13, the sample, the luminous material, the white colloidal particles, and the like that have been used for measurement in the luminescence detection unit 11 are discarded.

(2) Light Source Unit

The light source unit 21 emits light having a wavelength for exciting the luminous material 41 in the luminescence detection unit 11. The light source unit 21 may be a light source that emits irradiated light 22 having directivity and/or convergence. In addition, the light source may be selected depending on the type of the luminous material, and may be selected from, for example, a semiconductor laser, a light-emitting diode, and the like. Moreover, a condenser lens and/or the like may be provided between the light source unit 21 and the luminescence detection unit 11.

(3) Light Reception Unit

A light reception unit 31 receives emission light 32 emitted from the excited luminous material in the luminescence detection unit 11. The light reception unit may be implemented by, for example, a photodetector. Conventionally, non-enhanced emission light from the luminous material requires improvement into a highly sensitive light reception unit. However, the enhanced light emission having several tens of times higher intensity from the luminous material of the present technology allows a conventionally utilized light reception unit to be fully applicable.

Moreover, for example, a condenser lens may be provided between the light reception unit 31 and the luminescence detection unit 11 to receive light with higher sensitivity.

Note that a signal processing device, an analysis unit, and/or the like may further be included for controlling and processing an electrical signal induced by the light reception.

(4) Application of Substance Detection Apparatus

The present technology is also applicable to a technology, such as, for example, flow cytometry.

Examples thereof include an apparatus described below.

An apparatus includes a fluid (flow) system for arranging in a line a detection target labeled with a luminous material in the luminescence detection unit that is provided in place of a flow cell, and an optical system that irradiates each cell with laser light having an excitation wavelength, and detects light emitted from the luminous material.

In the luminescence detection unit, a laminar flow is formed of a sample containing the detection target labeled with the luminous material and a sheath fluid flowing around the sample. In this configuration, white colloidal particles are added to the sheath fluid in advance in an amount to provide a concentration ranging, for example, from 5 mass % to 20 mass %. Then, a small pressure difference is made between the sample and the sheath fluid to arrange in one line a plurality of the cells of the detection target labeled with the luminous material contained in the sample liquid. Irradiation of the luminescence detection unit under such condition with light having an excitation wavelength causes the cells of the detection target to traverse the path of the excitation light one by one. During this, the light emitted by excitation from each of the cells of the detection target is received by the light reception unit.

Such configuration can also provide the enhancing effect of the present technology on light emitted from the luminous material.

4. Luminescence Enhancer

The luminescence enhancer of the present technology contains, as an active ingredient, white colloidal particles having a particle size ranging from 0.1 µm to 1 µm.

Use of a luminescence enhancer can enhance light emitted when the luminous material is irradiated with light having an excitation wavelength. The luminescence enhancer is added in advance to the luminous material-containing sample before irradiation of the light having an excitation wavelength.

Before being added, the luminescence enhancer may be in a state suitable for storage, such as in a liquid, gel, solid, lyophilized, or other state, and may be diluted by water, a buffer, or the like before usage, and thus be prepared to have an appropriate concentration. In addition, an additive such as antiseptic agent, preservative, and/or the like may further be contained without reducing the effect of the present technology.

EXAMPLES

5. Experimental Examples (A) Increase in Fluorescence Intensity Provided by White Colloidal Particles The luminous material used was a group of fluorescent beads (trade name: Dragon Green, Bangs Laboratories Inc.) having an excitation wavelength of 480 nm and an emission wavelength of 520 nm. The white colloidal particles used were latex beads (trade name: Latex Microsphere, Thermo Fisher Scientific Inc.) having five submicron sizes (particle size: 0.06 µm, 0.10 µm, 0.24 µm, 0.64 µm, and 0.87 µm). Skim milk colloidal dispersion solutions were also used. Water was used as the dispersant and as the diluent for concentration preparation.

First, a sample ("Clear") containing no white colloidal particles and containing fluorescent beads was prepared.

Next, samples containing fluorescent beads at a concentration of 0.0001% w/v and containing latex beads respectively having the above five sizes each at a concentration of 10 percent by weight (wt %) were prepared.

In addition, samples that disperse fluorescent beads, and disperse skim milk respectively at concentrations of 5 wt %, 10 wt %, and 20 wt %, were prepared.

The samples were fed to the luminescence detection unit having an inner diameter of 300 µm in an optical axis direction, and 480 nm light was irradiated, and 520 nm light was then received.

The relative fluorescence intensity of each of the above samples with respect to the fluorescent signal of the sample ("Clear") containing no white colloidal particles, being defined as 1, was defined herein as specific fluorescence intensity.

Figure 2:
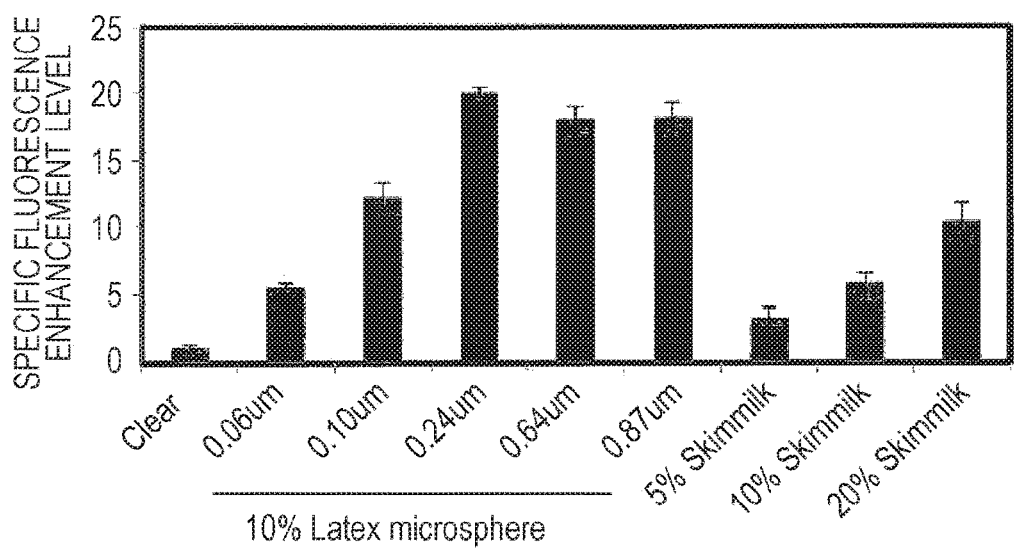
FIG. 2 is a graph illustrating an increase of the fluorescence intensity provided by white colloidal particles according to the present technology.

A graph plotting the specific fluorescence enhancement level of each sample is illustrated in FIG. 2.

A comparison with the sample "Clear" described above has shown that containing a colloidal dispersion solution in the luminescence detection unit causes the fluorescence intensity to be increased. Particularly, the sample dispersing the 0.24 µm latex beads has increased the specific fluorescence intensity to 20, meaning that the fluorescent signal has been increased 20 times higher.

(B) Study of Inner Diameter of Luminescence Detection Unit

Observations were made of change in the specific fluorescence intensity using different lengths (depths) of the flow channel along the optical axis direction of the luminescence detection unit of 120 µm, 240 µm, 360 µm, and 480 µm.

Each of the samples contained fluorescent beads identical to the fluorescent beads described in the section (A) above, and white colloidal particles, at a concentration of 10 wt %, identical to the 0.24 µm white colloidal particles described in the section (A) above. Each of the samples was prepared by serial dilution.

Figure 3:
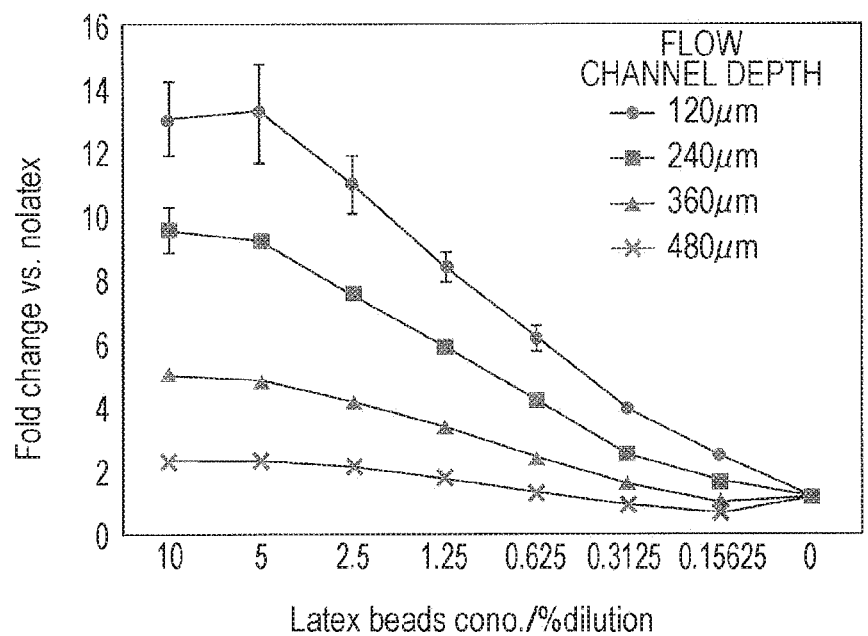
FIG. 3 is a graph illustrating a result of study of the inner diameter of a luminescence detection unit according to the present technology.

Results are illustrated in FIG. 3.

The study has shown that application of the present technology to a microchannel exhibits a higher fluorescence enhancing effect in a case where a signal is detected at a depth in a range of from several tens of micrometers to several hundreds of micrometers. The reason for this has seemed to be that an increase in the depth of the flow channel of the luminescence detection unit reduces the transparency.

(C) Study of Excitation Wavelength and Emission Wavelength of Fluorescent Beads

A study was made of the fluorescence enhancing effect observed in a colloidal solution of latex beads having a particle size of 0.24 µm used in the section (A) above at concentrations of 1 wt %, 5 wt %, and 10 wt %, using groups of nano-fluorescent beads respectively having different excitation wavelengths (Ex's) and different emission wavelengths (Em's). Three groups of fluorescent beads shown below were used.

Dragon Green (particle size: 54 nm, Ex480/Em520, Bangs Laboratories Inc.)

Flash Red (particle size: 190 nm, Ex660/Em690, Bangs Laboratories Inc.)

Europium (particle size: 200 nm, Ex365/Em610, Bangs Laboratories Inc.)

Figure 4:
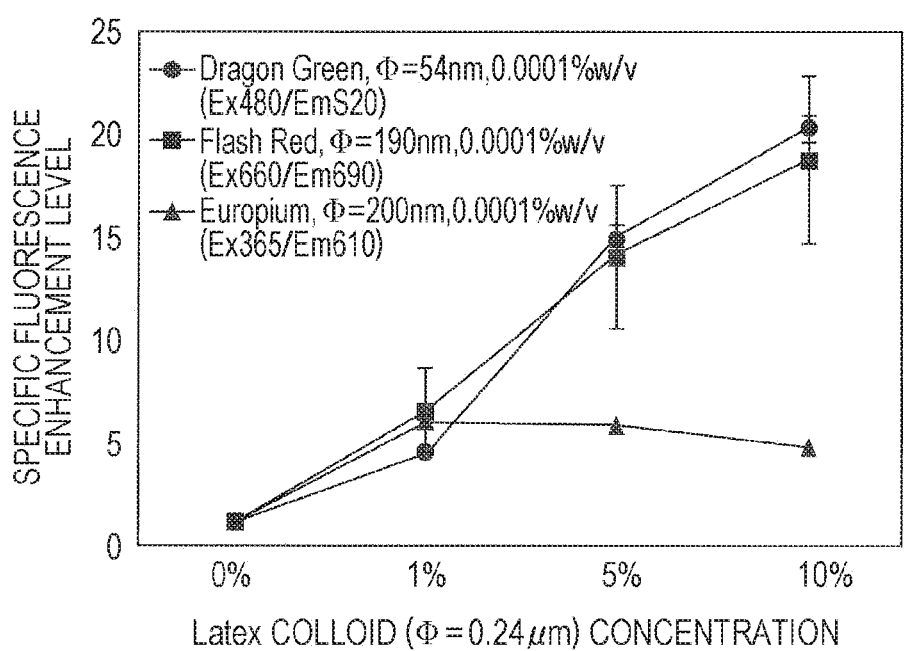
FIG. 4 is a graph illustrating a result of study of excitation wavelength and of emission wavelength of fluorescent beads according to the present technology.

FIG. 4 illustrates results obtained by irradiating with light having excitation wavelengths, and receiving light having emission wavelengths, respectively corresponding to the groups of fluorescent beads.

It has been shown that the groups of Ex480 nm/Em520 fluorescent beads and of Ex660/Em690 fluorescent beads both enhance fluorescence. In addition, the group of Ex365 nm/Em610 nm fluorescent beads having a UV light excitation wavelength has also exhibited a fluorescence enhancing effect.

(D) Study of Excitation Wavelength and Emission Wavelength of Fluorescent Molecules A study was made of the fluorescence enhancing effect of the white colloidal particles using fluorescent molecules instead of the fluorescent beads. Two groups of fluorescent molecules shown below were used.

Fluorescein (Ex480/Em520)

Rhodamine B (Ex552/Em588)

The white colloidal particles used were the latex colloidal solution at a concentration of 10 wt % used in the section (A) above.

The fluorescent molecules were prepared to provide a concentration of 10 µM.

Figure 5:
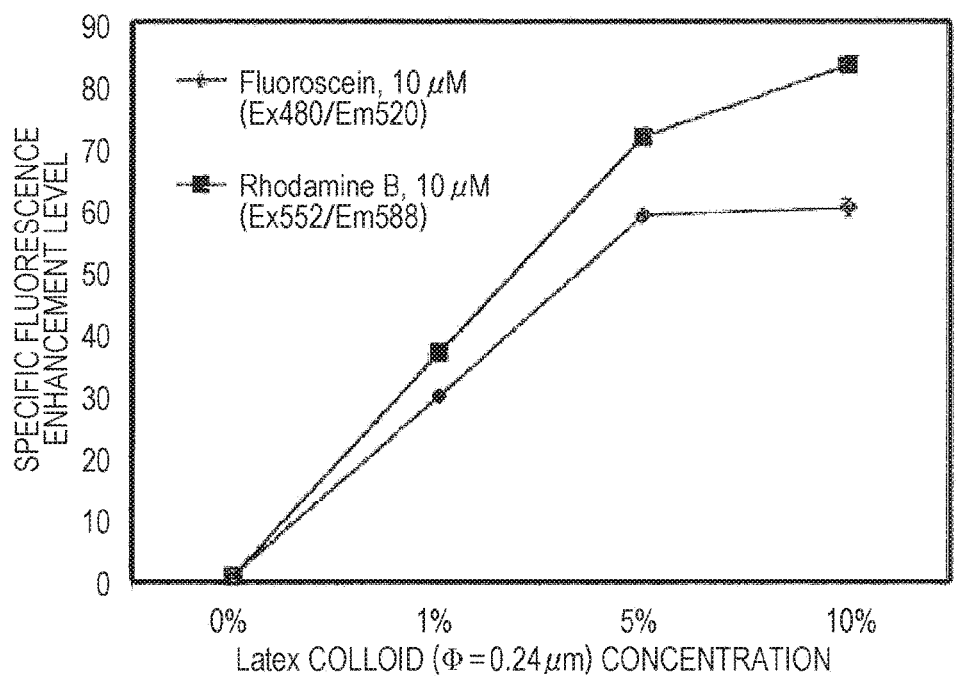
FIG. 5 is a graph illustrating a result of study of excitation wavelength and of emission wavelength of fluorescent molecules according to the present technology.

FIG. 5 illustrates results obtained by irradiating with light having excitation wavelengths, and receiving light having emission wavelengths, respectively corresponding to the groups of fluorescent molecules.

A fluorescence enhancing effect waterfall than that of the fluorescent beads has been observed; Rhodamine B (Ex552/Em588) has exhibited an increase in fluorescence enhancing effect by 80 times or more.

Note that the present technology can also have the configurations described below.

[1] A method for enhancing luminescence of a luminous material, the method including:

holding, in a luminescence detection unit, the luminous material and a white colloidal particle both contained in a liquid; and irradiating the luminescence detection unit with light, in which the luminescence detection unit has an inner diameter of 300 µm or less in an optical axis direction.

[2] The method according to [1], in which the light is UV light and/or visible light.

[3] The method according to [1] or [2], in which the luminous material is a fluorescent pigment or a fluorescent bead.

[4] The method according to any of [1] to [3], in which the colloidal particle is contained in the liquid in the luminescence detection unit at a concentration ranging from 5 percent by mass (mass %) to 20 mass %.

[5] The method according to any of [1] to [4], in which the colloidal particle has a particle size ranging from 0.1 μm to 1 μm.

[6] The method according to any of [1] to [5], in which the colloidal particle is at least one type of particle selected from the group consisting of latex, acryl, silicone, polyurethanes, polyvinyls, polylactic acid, polyacetic acid, PVDF, PFA, PTFE, polycarbonates, polyolefins, polyethylene glycols, polyethylenes, nylons, lipids, proteins, nucleic acids, liposomes, and microorganism cells.

[7] A substance detection method including:
holding, in a luminescence detection unit, a detection target material labeled with a luminous material, and a white colloidal particle, both contained in a liquid; and
irradiating the luminescence detection unit with light,
in which the luminescence detection unit has an inner diameter of 300 μm or less in an optical axis direction.

[8] A substance detection apparatus including:
a luminescence detection unit having an inner diameter of 300 μm or less in an optical axis direction, the luminescence detection unit capable of holding a luminous material and a white colloidal particle both contained in a liquid;
alight source unit for irradiating the luminescence detection unit with light; and
a light reception unit that receives light emitted from the luminous material.

[9] A luminescence enhancer containing, as an active ingredient, a white colloidal particle having a particle size ranging from 0.1 μm to 1 μm.

REFERENCE SIGNS LIST

11 Luminescence detection unit
12 Inlet
13 Outlet
14 Flow channel
15 Flow channel
16 Sample feed port
17 White colloidal particle feed port
21 Light source unit
22 Irradiated light
31 Light reception unit
32 Emission light
41 Luminous material
51 White colloidal particle
61 Inner diameter

The invention claimed is:

1. A method, comprising:
holding, in a luminescence detection unit, a luminous material and a white colloidal particle, wherein both the luminous material and the white colloidal particle are contained in a liquid, and wherein a shape of the luminescence detection unit is one of a cylinder, a circular truncated cone, an inverted circular truncated cone, an elliptic cylinder, an elliptic column, an inverted elliptic truncated cone, a sphere, or an ellipsoid; and
irradiating the luminescence detection unit with light,
wherein the shape of the luminescence detection unit has an inner diameter of 300 μm or less in an optical axis direction.

2. The method according to claim 1, wherein the light is at least one of UV light or visible light.

3. The method according to claim 1, wherein the luminous material is one of a fluorescent pigment or a fluorescent bead.

4. The method according to claim 1, wherein the white colloidal particle is contained in the liquid in the luminescence detection unit at a concentration ranging from 5 percent by mass (mass %) to 20 mass %.

5. The method according to claim 1, wherein the white colloidal particle has a particle size ranging from 0.1 μm to 1 μm.

6. The method according to claim 1, wherein the white colloidal particle is at least one type of particle selected from the group consisting of latex, acryl, silicone, polyurethanes, polyvinyls, polylactic acid, polyacetic acid, PVDF, PFA, PTFE, polycarbonates, polyolefins, polyethylene glycols, polyethylenes, nylons, lipids, proteins, nucleic acids, liposomes, and microorganism cells.

7. A substance detection method, comprising:
holding, in a luminescence detection unit, a detection target material labeled with a luminous material, and a white colloidal particle, wherein both the luminous material and the white colloidal particle are contained in a liquid, and wherein a shape of the luminescence detection unit is one of a cylinder, a circular truncated cone, an inverted circular truncated cone, an elliptic cylinder, an elliptic column, an inverted elliptic truncated cone, a sphere, or an ellipsoid; and
irradiating the luminescence detection unit with light,
wherein the shape of the luminescence detection unit has an inner diameter of 300 μm or less in an optical axis direction.

8. A substance detection apparatus, comprising:
a luminescence detection unit configured to hold a luminous material and a white colloidal particle, and wherein both the luminous material and the white colloidal particle are in a liquid, wherein a shape of the luminescence detection unit is one of a cylinder, a circular truncated cone, an inverted circular truncated cone, an elliptic cylinder, an elliptic column, an inverted elliptic truncated cone, a sphere, or an ellipsoid, and wherein the shape of the luminescence detection unit has an inner diameter of 300 μm or less in an optical axis direction;
a light source unit configured to irradiate the luminescence detection unit with light; and
a light reception unit configured to receive light emitted from the luminous material.

9. A luminescence enhancer, containing:
a white colloidal particle, wherein the white colloidal particle is an active ingredient having a particle size ranging from 0.1 μm to 1 μm, and wherein the white colloidal particle enhances light.

* * * * *